United States Patent
Bollinger et al.

(10) Patent No.: US 6,635,415 B1
(45) Date of Patent: *Oct. 21, 2003

(54) NITRIC OXIDE GAS DETECTOR

(75) Inventors: Mark J. Bollinger, Golden, CO (US);
John W. Birks, Longmont, CO (US);
Jill K. Robinson, Laramie, WY (US)

(73) Assignee: 2B Technologies, Inc., Golden, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/552,285

(22) Filed: Apr. 19, 2000

Related U.S. Application Data (63) Continuation-in-part of application No. 09/037,311, filed on Mar. 9, 1998, now Pat. No. 6,100,096.

(51) Int. Cl.[7] ............................. G01N 33/00; C12Q 1/00
(52) U.S. Cl. .................................. 435/4; 422/81; 422/82; 422/83; 422/88; 436/106; 436/117; 436/118; 436/172; 436/175; 436/177; 436/178; 436/116
(58) Field of Search .......................... 422/81–83, 88, 422/82.05, 91; 436/106, 116, 117, 118, 172, 175, 177, 178, 181; 435/4

(56) References Cited

U.S. PATENT DOCUMENTS

| | | |
|---|---|---|
| 3,659,100 A | 4/1972 | Anderson et al. |
| 3,679,312 A | 7/1972 | Mansberg |
| 3,700,896 A | 10/1972 | Anderson et al. |
| 3,710,107 A | 1/1973 | Warren et al. |
| 3,797,999 A | 3/1974 | Witz et al. |
| 3,940,250 A | 2/1976 | Plakas et al. |
| 4,268,279 A | 5/1981 | Shindo et al. |
| 4,765,961 A | 8/1988 | Schiff et al. |
| 4,912,051 A | 3/1990 | Zaromb |
| 4,942,135 A | 7/1990 | Zaromb |
| 5,094,817 A | 3/1992 | Aoki et al. |
| 5,271,894 A | 12/1993 | Kozakura et al. |
| 5,424,216 A | 6/1995 | Nagano et al. |
| 5,434,085 A | 7/1995 | Capomacchia et al. |
| 5,451,788 A | 9/1995 | Pollack |
| 6,100,096 A | * 8/2000 | Bollinger et al. ............ 436/116 |

FOREIGN PATENT DOCUMENTS

GB 1515421 * 6/1978

OTHER PUBLICATIONS

M. R. Burkhardt et al, Atmos. Environ. 1988, 22, 1575–1578.*
S. M. Gordon et al, Meas. Toxic Relat. Air Pollut., Proc. Spec. Conf. 1997, 2, 711–720.*
G. L. Hutchinson et al, Atmos. Environ. 1999, 33, 141–145.*
J.K. Robinson et al, Anal. Chem. 1999, 71, 5131–5136.*
Maria Cecilia Carreras et al., "Kinetics of nitric oxide and hydrogen peroxide production and formation of peroxynitrite during the respiratory burst of human neutrophils," FEBS Letters 341 (1994) 65–68.

(List continued on next page.)

*Primary Examiner*—Arlen Soderquist
(74) *Attorney, Agent, or Firm*—Rick Martin; Patent Law Offices of Rick Martin, P.C.

(57) ABSTRACT

The concentration of nitric oxide in a gas is determined by oxidizing NO to $NO_2$ and then measuring the concentration of $NO_2$ in the gas, which is proportional to the concentration of NO. Preferably, gaseous $NO_2$ molecules diffuse through a plurality of capillary membrane fibers and undergo a chemiluminescent reaction with a reagent flowing within; the light from the reaction is measured to determine $NO_2$ concentration. In another aspect of a preferred embodiment, gas is passed through a scrubber before the concentration of $NO_2$ is measured, in order to substantially remove carbon dioxide and ambient $NO_2$ from the gas without substantially affecting the concentration of nitric oxide therein.

1 Claim, 4 Drawing Sheets

OTHER PUBLICATIONS

Kikuchi et al., "Detection of Nitric Oxide Production from a Perfused Organ by a Luminol–H2O2 System," Anal. Chem. 1993, 65, 1794–1799.

Kikuchi et al., "Real Time Measurement of Nitric Oxide Produced ex Vivo by Luminol–H2O2 Chemiluminescene Method," 268 J. Biol. Chem. 23106–23110 (1993).

Radi et al., "Peroxynitrite–induced luminol chemiluminescence," 290 Biochem. J. 51–57 (1993).

Kelly et al., "An Assessment of the Luminol Chemiluminescence Technique for Measurement of N02 in Ambient Air," 24A Atmospheric Environment 2397–2403 (1990).

Schiff et al., "Atmospheric Measurements of Nitrogen Dioxide with a Sensitive Luminol Instrument," 30 Water, Air and Soil Pollution 105–114 (1986).

Wendel et al., "Luminol–Based Nitrogen Dioxide Detector," 55 Anal. Chem. 937–940 (1983).

Maeda et al., "Chemiluminescence Method for the Determination of Nitrogen Dioxide," 52 Anal. Chem. 307–311 (1980).

T. Fujiwara et al., Spectrochim. Acta Rev. 1990, 13, 399–406.

M. A. Lapack et al., Anal. Chem. 1991, 63, 1631–1637.

A. B. Shelekhin et al., J. Membrane Sci. 1992, 73, 73–85.

R.S. Lewis et al., Biol. Mass Spectrom. 1993, 22, 45–52.

D.P. Lucero, ISA Trans. 1977, 16, 71–80.

J.R. Poulsen et al., Chromatographia 1986, 22, 231–234.

D.A. Hollowell et al., Anal. Chem. 1986, 58, 1524–1527.

T. Aoki et al., Chem. Abstr. 1987, 107, 161193h.

T. Aoki et al., Chem. Abstr. 1988, 108, 156173t.

Y. Kanada et al., Anal. Chem. 1990, 62, 2084–2087.

J. L. P. Pavon et al., Anal. Chem. 1992, 64, 923–929.

H. Zhao et al., Am. J. Physiol, 1994, 267, C385–C393.

J. S. Beckman et al., Methods 1995, 7, 35–39.

A. J. Dunham et al., Anal. Chem. 1995, 67, 220–224.

G. E. Collins et al., "Field Screening Methods Hazard Wastes Toxic Chem., Pro. Int. Symp." 1995, vol. 1, pp. 196–203.

X. Zhou et al., Anal. Chem 1996, 68, 1748–1754.

A. Aneman et al. Am. J. Physiol. 1996, 271, G1039–G1042.

* cited by examiner

NITRIC OXIDE GAS DETECTOR

This is a continuation-in-part of application Ser. No. 09/037,311, filed on Mar. 9, 1998, now U.S. Pat. No. 6,100,096.

FIELD OF THE INVENTION

This invention generally relates to gas analysis, and more particularly to the detection and measurement of nitric oxide in exhaled human breath.

BACKGROUND OF THE INVENTION

At present, gaseous nitric oxide (NO) is most commonly measured by mixing a gas sample with ozone gas at low pressures. When a nitric oxide molecule reacts with an ozone ($O_3$) molecule, it forms nitrogen dioxide ($NO_2$) and oxygen ($O_2$) and emits a photon in the process. This photon possesses a red or near-infrared wavelength. The concentration of nitric oxide in the gas sample is thus determined by measuring the intensity of those photons. However, red and near-infrared wavelengths are not detected efficiently by standard photodetecting devices such as photomultiplier tubes and photodiodes. Consequently, special photodetector devices that are more sensitive to red light must be used. These devices must be cooled to subambient levels to reduce background noise from thermal effects. These special devices and their cooling requirements add cost and complexity over that required to measure visible light.

In addition, an ozone-based nitric oxide gas detector requires a vacuum pump and a method for making ozone, which is typically a high-voltage electrical discharge. As a result, ozone-based detectors are generally bulky and complex, and require a significant amount of electricity to operate. The high voltage required to operate an ozone-based detector can pose a safety risk to the user and to those nearby. Government regulations restrict allowable ozone exposure, making it difficult to use ozone-based nitric oxide gas detectors in the workplace. Furthermore, ozone is a toxic gas, and it must be vented or destroyed after use. Because ozone is a pollutant, environmental regulations may prohibit venting the ozone in many areas, forcing the user of an ozone-based detector to destroy the ozone after use. Destruction of the ozone adds an additional step, and additional cost, to the nitric oxide measurement process.

Gaseous nitric oxide may also be detected by placing a gas sample in contact with an alkaline luminol solution containing hydrogen peroxide. As with the ozone-based method of detection, the chemical reaction between nitric oxide and the luminol solution results in the emission of photons. Unlike the ozone-based method of detection, these photons possess wavelengths in the more energetic end of the visible light spectrum. While the luminol-based method of detection overcomes some of the problems of ozone-based detection, it possesses drawbacks of its own. One drawback is toxicity of the chemicals used to detect ozone. Luminol, as well as bases which may be used to render the luminol solution alkaline, may be toxic if ingested or inhaled. Where human breath is to be measured, precautions must be taken to prevent such liquids, or fumes which may arise from them, from traveling through the measuring apparatus into the lungs of the person whose breath is being measured. Such precautions may cause the measurement process to be less efficient or in other ways interfere with the measurement of nitric oxide within exhaled human breath.

Another drawback is interference from the presence of carbon dioxide. When measuring atmospheric nitric oxide, carbon dioxide levels are typically too low (300–400 parts per million (PPM), which is 0.03–0.04 percent) to interfere with the measurement. However, carbon dioxide typically constitutes several percent of exhaled human or animal breath. This amount of carbon dioxide is orders of magnitude greater than the amount present in the atmosphere, and interferes with the detection and measurement of nitric oxide in human or animal breath when using a chemiluminescence-based detector. This interference primarily occurs in three ways. First, at a concentration of several percent, carbon dioxide reacts with the luminol solution to produce the same number of photons produced by the reaction of several parts per billion (PPB) of nitric oxide with luminol, tricking the detector into registering the presence of several PPB of nitric oxide which is not present in the sample. Second, carbon dioxide is known to react with a key intermediate in the nitric oxide/luminol reaction, ionic peroxynitrite ($ONOO^-$). This reaction reduces the response of the luminol solution to nitric oxide, causing the detector to measure less nitric oxide than is actually present. Third, some gaseous carbon dioxide will dissolve in the alkaline luminol solution, changing its pH and thereby reducing the standing background signal of the luminol solution.

SUMMARY OF THE INVENTION

In one aspect of a preferred embodiment, the concentration of nitric oxide in a gas is determined by oxidizing NO to $NO_2$, then measuring the concentration of $NO_2$ in the gas, which is proportional to the concentration of NO and from which the concentration of NO is determined. Preferably, gaseous NO is converted to $NO_2$ using chromium trioxide as a catalyst. In a particular embodiment, glass beads are coated with chromium trioxide, and the gas flows through the space between the beads. Contact between gaseous NO and the coated beads oxidizes the NO to form gaseous $NO_2$.

In another aspect of a preferred embodiment, gas-permeable capillary membrane fibers transport a reagent solution through a chamber containing a gas to be analyzed. The capillary membrane fibers are constructed of a material porous enough, and are thin enough, to allow gaseous $NO_2$ molecules to diffuse through and undergo a chemiluminescent reaction with the reagent within. The capillary membrane fibers are translucent, allowing photons emitted by the chemiluminescent reaction to pass through and be detected by a photodetector.

In another aspect of a preferred embodiment, gas is passed through a scrubber before entering the capillary membrane fibers. The scrubber removes carbon dioxide and ambient $NO_2$ from the gas without substantially affecting the concentration of nitric oxide in the gas.

In another aspect of a preferred embodiment, gas to be analyzed is passed through a moisture exchanger to control its humidity. In another aspect, the moisture exchanger is located in a humidity-controller chamber. In a further aspect of a preferred embodiment, a humidity control unit including a water-absorbing material that is substantially saturated with water accepts dry gas at a pressure above atmospheric pressure, then discharges that gas at atmospheric pressure into the chamber, thereby controlling the humidity within the chamber.

In an aspect of a second preferred embodiment, nitric oxide is measured directly, without conversion to $NO_2$ and without the use of a scrubber. The nitric oxide molecules penetrate the walls of capillary membrane fibers and undergo a chemiluminescent reaction with a reagent inside those fibers. In a further aspect of another preferred embodiment, the reagent is buffered at an alkaline pH and mixed with the enzyme carbonic anhydrase to reduce the measurement error that may be caused by the presence of carbon dioxide gas.

In an aspect of an alternate embodiment, a gas-permeable membrane within a plenum separates a first space containing gases to be measured from a second space containing a reagent. The membrane is thin enough and porous enough to enable gaseous nitric oxide molecules to pass through and undergo a chemiluminescent reaction with the reagent in the second space. The plenum is translucent, allowing photons emitted by the chemiluminescent reaction to pass through and be detected by a photodetector.

In an aspect of another alternate embodiment, the chemiluminescent reactant is not present in the reagent when the gaseous nitric oxide is exposed to the reagent. Rather, the chemiluminescent reactant is added in a second chamber, where the light produced by the chemiluminescent reaction is measured by a photodetector. Optionally, a carbonic anhydrase solution may be added in this second chamber to minimize the effect of carbon dioxide when nitric oxide is being measured in an environment containing a high concentration of carbon dioxide.

DETAILED DESCRIPTION OF THE PREFERRED EMBODIMENTS

Figure 1:
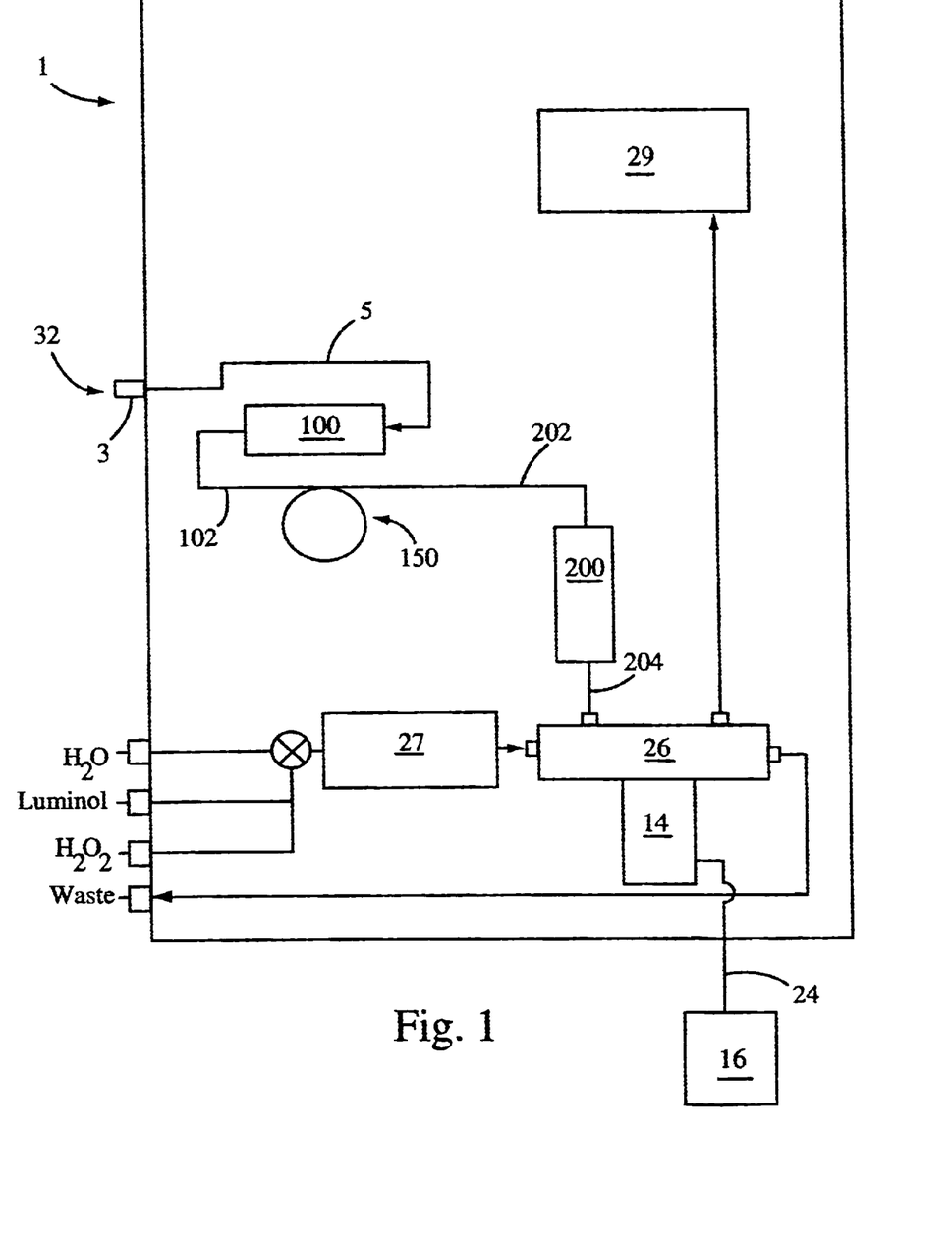
FIG. 1 is a schematic representation of a nitric oxide gas detector.

Referring to FIG. 1, a schematic view of a nitric oxide gas detector 1 is shown. A gas 32 to be sampled enters the nitric oxide gas detector through an entrance port 3. Preferably, the entrance port 3 is in flow communication with a scrubber 100, either directly or via a hose such as the entrance hose 5.

The scrubber 100 minimizes the presence of carbon dioxide in the gas to be sampled. Preferably, the scrubber 100 is a length of tube filled with silica particles coated with sodium hydroxide. In a preferred embodiment, ASCARITE® brand silica particles coated with sodium hydroxide, sold by Thomas Scientific of Swedesboro, N.J., are used. The scrubber 100 removes carbon dioxide from the gas by the reaction:

$$CO_2 + 2NaOH \rightarrow Na_2CO_3 + H_2O \quad (1)$$

In a preferred embodiment, substantially one gram of ASCARITE® brand silica particles coated with sodium hydroxide is placed in a tube having an internal diameter of substantially 0.25 inch and a length of substantially two inches. The gas 32 is directed through the scrubber 100. The individual particles of silica particles coated with sodium hydroxide are held in the tube with a screen or other structure known in the art that allows the gas 32 into the scrubber 100 but prevents substantially all of the particles from escaping from the scrubber 100. These particles are large enough for the gas 32 to pass around, but small enough to allow substantially all of the gas 32 to contact the sodium hydroxide coating. In a preferred embodiment; the flow rate through the scrubber 100 is substantially 200 ml/minute when used with a scrubber 100 having a substantially two-inch length. This flow rate allows the gas 32 to remain in the scrubber 100 long enough for carbon dioxide present in the gas 32 to be substantially removed. If the gas 32 to be sampled is flowing at greater than 200 ml/minute, a side stream may be advantageously pulled from it at substantially 200 ml/minute; that side stream of gas 32 is routed into the scrubber 100. The plumbing required to pull a side stream from a main flow can be easily built by one of ordinary skill in the art. It will be apparent to one of ordinary skill in the art that if the length of the tube is changed, the flow rate through the scrubber 100 may be correspondingly changed by the operator, so long as the carbon dioxide present in the gas 32 is still substantially removed by the scrubber 100. It will also be apparent that a greater or lesser amount of silica particles coated with sodium hydroxide may be used in the scrubber 100, so long as the carbon dioxide present in the gas is substantially removed.

Experiments with gases containing concentrations of carbon dioxide similar to those found in human breath have demonstrated that carbon dioxide gas is substantially eliminated by the scrubber 100, while the concentration of NO is reduced by no more than 0.5 parts per billion. Thus, the scrubber 100 removes carbon dioxide from the gas to be sampled, while having no appreciable effect on the concentration of NO. The scrubber 100 also has the effect of removing substantially all of the nitrogen dioxide from the gas 32. The sodium hydroxide coating the silica particles is a strong base. Both carbon dioxide and nitrogen dioxide are acidic gases, which react with sodium hydroxide. The removal of nitrogen dioxide from the gas 32 is beneficial, as will be further understood below. Typically, a scrubber 100 containing 1 gram of ASCARITE® brand silica particles coated with sodium hydroxide has sufficient capability to reduce or minimize carbon dioxide and nitrogen dioxide in five to fifteen gas samples. It is within the scope of the preferred embodiment to provide a scrubber 100 having a quantity of silica particles coated with sodium hydroxide adequate for a single test, after which the scrubber 100 is discarded. Such a single-use scrubber 100 may be incorporated into a mouthpiece, facemask, or other breath collector into which a subject breathes for collection of the breath gas to be sampled.

Control of the humidity of the gas 32 is not required for the nitric oxide gas detector 1 to function; it can be calibrated to function at any humidity. Therefore, the presence of the moisture exchanger 150 in the nitric oxide gas detector 1 is optional. However, the operation of the nitric oxide gas detector is more efficient at a humidity level under 30%, and advantageously at substantially 13%, as will be explained further later. In a preferred embodiment, humidity modification means are provided to control the humidity level of the gas 32 to such advantageous levels. In one embodiment, the humidity modification means is a moisture exchanger 150. The gas 32 passes from the scrubber 100 to a moisture exchanger 150 through a hose 102 or other means of flow communication. The moisture exchanger 150 substantially equilibrates the moisture content of the gas 32 with the ambient humidity. Typically, the moisture exchanger 150 is used when exhaled breath is analyzed, as the moisture content of exhaled breath is generally higher than ambient humidity. The moisture exchanger 150 is preferably composed of NAFION® brand moisture exchange tubing, manufactured by Perma Pure of Toms River, N.J. However, any other tubing may be used that allows moisture exchange with the ambient air. In a preferred embodiment, the moisture exchanger 150 comprises a 24-inch length of NAFION® brand moisture exchange tubing having an outside diameter of ⅛ inch.

Figure 1A:
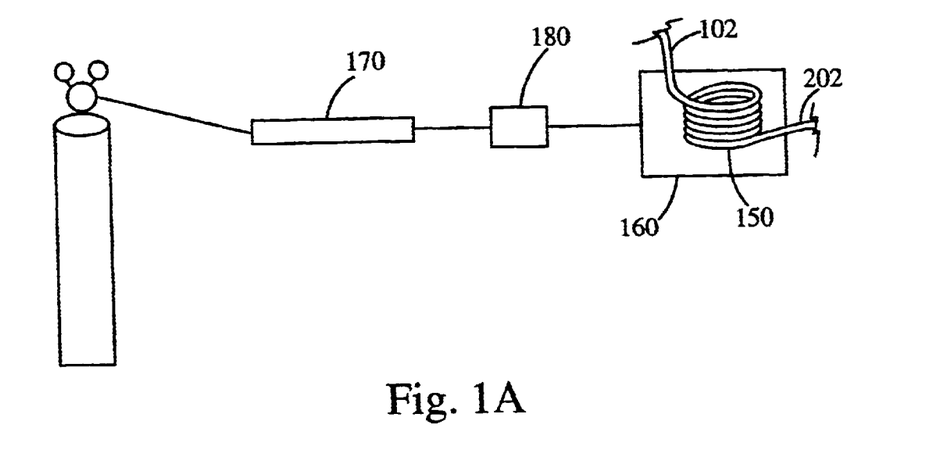
FIG. 1A is a schematic representation of a humidity control unit and moisture exchanger.

Referring to FIG. 1A, the moisture exchanger 150 is advantageously located inside a chamber 160, inside which the humidity is also controlled at a level below ambient in any effective manner. The use of such a chamber 160 is particularly desirable if ambient humidity is greater than 30%. In a preferred embodiment, a humidity control unit 170 is used to control the humidity in the chamber 160. A dry gas, as from a cylinder or similar source, enters the humidity control unit 170 at a pressure above atmospheric pressure. The humidity control unit 170 operates on the principle that a dry gas at a pressure above atmospheric pressure holds less water than the same gas at atmospheric pressure. The humidity control unit 170 is preferably a hollow structure containing a water-absorbing material, such as but not limited to cotton. In a preferred embodiment, the humidity control unit 170 is a tube substantially ten inches long and two inches in inside diameter, filled with cotton, and constructed to withstand at least 150 psi as a safety measure. The water-absorbing material is preferably substantially saturated with water. Preferably, the dry gas enters the humidity control unit 170 at substantially 60–80 psi. Water in the water-absorbing material evaporates into that gas. The entry of gas into the humidity control unit 170 is stopped, and a flow controller 180 in flow communication with the humidity control unit 170 is opened. The flow controller 180 allows the gas inside the humidity control unit 170 to escape, in the process decreasing to atmospheric pressure. When that gas is reduced to atmospheric pressure, its humidity is approximately fifteen percent. The flow controller 180 is in flow communication with the chamber 160, allowing that gas at approximately fifteen percent humidity to enter the chamber 160 and contact the outer surface of the tubing of the moisture exchanger 150. Humidity from the gas 32 inside the tubing of the moisture exchanger 150 diffuses through the tubing into the chamber, due to the difference in water content in the gas inside the tubing and outside the tubing. When the gas 32 exits the moisture exchanger 150, its humidity level has been reduced closer to a desired level. It will also be appreciated that the chamber 160 would also humidify very dry gas 32 having less than substantially fifteen percent humidity; humidity would diffuse from the chamber 160 into the tubing of the moisture exchanger 150. While a preferred embodiment of a moisture exchanger 150 and humidity control unit 170 have been disclosed, other components and methods for controlling the humidity of the gas 32 will be apparent to one of ordinary skill in the art.

The gas 32 passes out of the moisture exchanger 150 to a converter unit 200 through a hose 202 or other structure that allows flow communication between them. If the humidity modification means is not used, the scrubber 100 is connected to the converter unit 200 through a hose 202 or other structure that allows flow communication between them. In a preferred embodiment, the converter unit 200 includes glass beads coated with chromium trioxide and packed in a length of glass tubing. The glass beads are preferably between 0.7 mm and 1.0 mm in diameter; their diameters need not be uniform. Advantageously, the coated glass beads have a mass of substantially 2 grams, and are placed in substantially 4 inches of glass tubing having an internal diameter of ⅜ inch. In a preferred embodiment, the glass beads are held in place with steel wool. However, the glass beads may be held in place by other structures that do not substantially interfere with the flow of the gas 32 through the converter unit 200 and that do not substantially react with the gas 32, such as but not limited to fiberglass or quartz wool. Such structures will be apparent to one having ordinary skill in the art.

The glass beads may be coated with chromium trioxide ($CrO_3$) by soaking the glass beads in a 20% by weight aqueous solution of $CrO_3$ for 10 minutes. The glass beads are then filtered from the solution and dried in an oven at substantially 60 degrees C. This process will result in the deposition of approximately 30 milligrams of $CrO_3$ on the glass beads. Of course, other methods may be used for coating the glass beads with chromium trioxide. As the gas 32 is passed through the converter unit 200, the nitric oxide in the gas 32 oxidizes as it contacts the chromium trioxide on the glass beads, becoming nitrogen dioxide. The removal of ambient $NO_2$ by the scrubber 100, as discussed above, prevents ambient $NO_2$ from causing error. Because ambient $NO_2$ has been substantially removed from the gas 32 before it enters the conversion unit 200, substantially all of the nitrogen dioxide exiting the converter unit 200 has resulted from the conversion of NO to $NO_2$.

The converter unit 200 is utilized in a preferred embodiment because $NO_2$ is more readily detected by the nitric oxide gas detector 1 than NO. By converting substantially all of the NO in the gas 32 to $NO_2$, then measuring the concentration of $NO_2$, the efficiency and accuracy of the measurement is improved. The nitric oxide gas detector 1 is calibrated by the user such that those measurements of $NO_2$ concentration are readily and accurately converted to measurements of NO concentration.

Figure 2:
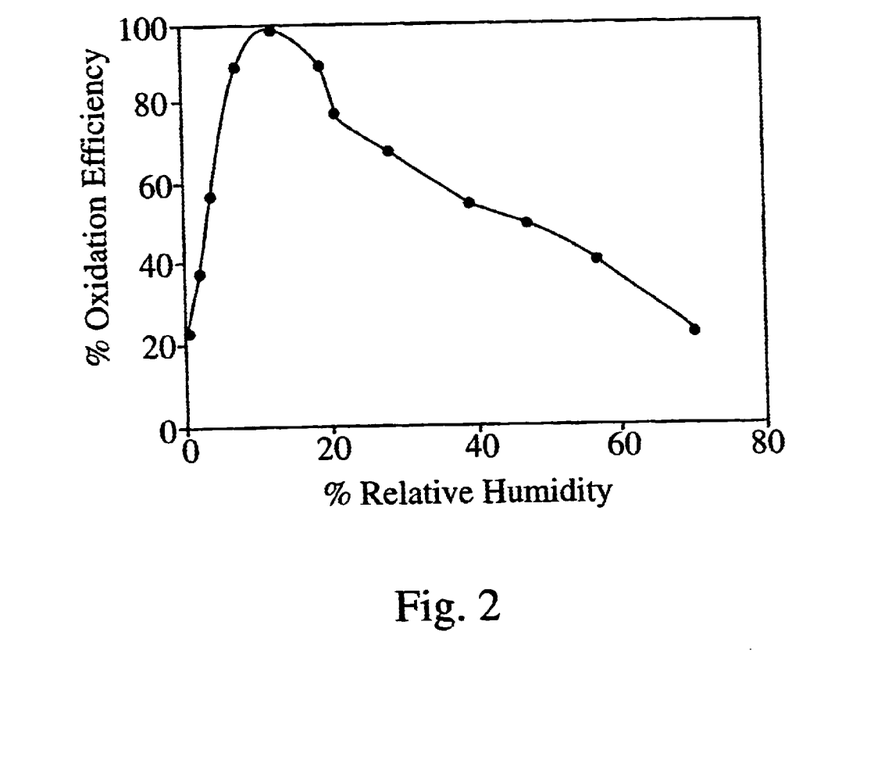
FIG. 2 is a graph showing the relationship between the ambient relative humidity and the oxidation efficiency of a converter unit.

The efficiency with which the converter unit 200 converts NO to $NO_2$ is a function of the relative humidity of the gas 32. The maximum efficiency of the converter unit 200 has been measured to be substantially 99% at a relative humidity of substantially 13%. Thus, the humidity of the gas 32 is advantageously controlled to be within a few percentage points of 13%. Such control can be achieved with various devices and methods that will be apparent to one of ordinary skill in the art, of which the moisture exchanger 150 is one. FIG. 2 shows the relationship between the relative humidity of the gas 32 and the conversion efficiency in graphical form. Thus, the humidity of the gas 32 may be controlled to increase or optimize the conversion efficiency. It will be appreciated that the gas 32 preferably flows through the converter unit 200 at a rate that allows for nitric oxide conversion at a substantial fraction of the efficiency given by FIG. 2 at a given humidity.

Figure 3:
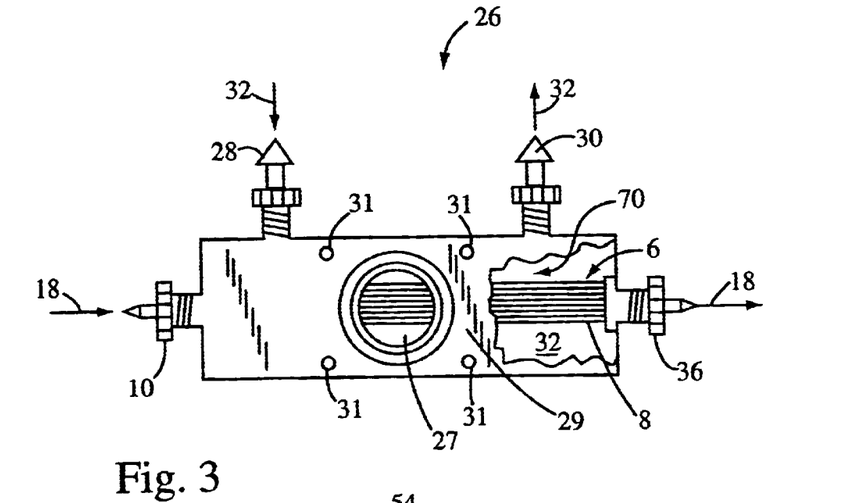
FIG. 3 is a perspective view of a gas exchange module within the nitric oxide gas detector.

The gas 32 passes out of the converter unit 200 to a gas exchange module 26 through a hose 204 or other structure that allows flow communication between the converter unit 200 and the gas exchange module 26. Referring to FIGS. 1 and 3, a gas exchange module 26 is seen. The gas exchange module 26 is substantially opaque, and includes a window 27 that is translucent or transparent. The gas 32 enters the gas exchange module 26 through an inlet port 28. The inlet port 28 leads to a chamber 70 within the gas exchange module 26. The outlet port 30 is preferably located away from the inlet port 28 such that the gas 32 can enter the chamber 70 and substantially replace ambient gases previously reposing in the chamber 70. Referring to FIG. 1, to produce a flow of gas 32 into the inlet port 28, a pump 29 or other suction device may be attached to an outlet port 30 in the gas exchange module 26. Alternatively, the gas exchange module 26 may be placed in line with or in parallel with a gas line or duct, such that the flow of gas through such gas line or duct impels the gas 32 into the inlet port 28 and out of the outlet port 30. Alternatively, some applications of this device, such as atmospheric measurements or some types of medical applications, may not require the active production of gas flow into the gas exchange module 26, in which case the gas 32 would enter the gas exchange module 26 through either the inlet port 28 or the outlet port 26 due to gas motion in the ambient environment.

Referring back to FIG. 3, after the gas 32 has entered the chamber 70, the gas 32 comes into contact with one or more capillary membrane fibers 8. Preferably, one or more capillary membrane fibers 8 are organized into a fiber bundle 6. However, the capillary membrane fibers 8 may extend into the chamber 70 independently of one another. Preferably, the fiber bundle 6 is composed of approximately fifty capillary membrane fibers 8. These capillary membrane fibers 8 are preferably substantially parallel within the fiber bundle 6, but they may be twisted or wrapped together into a fiber bundle 6. Preferably, the capillary membrane fibers 8 extend through substantially the entire length of the gas exchange module 26. Each capillary membrane fiber 8 is connected at one end to a fluid inlet connector 10 and at the other end to a fluid outlet connector 36. One side of the fluid inlet connector 10 is connected to one end of each of the capillary membrane fibers 8 that compose the fiber bundle 6. Preferably, the connection between each capillary membrane fiber 8 and the fluid inlet connector 10 is accomplished by epoxy adhesive. However, the connection may be accomplished by any means that do not substantially restrict flow of a reagent 18 from the fluid inlet connector 10 into the capillary membrane fibers 8. The other side of the fluid inlet connector 10 possesses at least one opening for the reagent 18 to enter, and provides for more convenient operation by an operator, who does not have to make individual small-scale connections to each capillary membrane fiber 8. The capillary membrane fibers 8 attach to the fluid outlet connector 36 in the same manner, and the fluid outlet connector 36 also possesses at least one opening for the reagent 18 to exit.

The reagent 18 flows into the gas exchange module 26 through the fluid inlet connector 10, from there flowing into the capillary membrane fibers 8 composing the fiber bundle 6. The preferred flow rate of the reagent 18 is 0.5–5.0 ml/min. Advantageously, the flow rate is 1.25 ml/min. Preferably, the pump 29 provides control over the flow rate of the reagent 18. Alternately, the reagent 18 may be induced to flow into the gas exchange module 26 by gravity, by pumping, by suction, or by any other means which can induce a sufficient flow rate of the reagent 18.

Each capillary membrane fiber 8 is composed of a porous material sufficiently thin to allow gaseous $NO_2$ molecules to pass through into the interior space within the capillary membrane fiber 8, but not so thin or porous that the reagent 18 leaks through the capillary membrane fiber 8. Each capillary membrane fiber 8 must also be thick enough to prevent rupture as the reagent 18 flows through. The pressure within each capillary membrane fiber 8 is a function of the flow rate of the reagent 18. To satisfy these considerations, in a preferred embodiment each capillary membrane fiber 8 is made of polypropylene and has an outer diameter of substantially 380 microns, a wall thickness of 50 microns, and a pore size of 0.2 microns.

Gaseous nitrogen dioxide in the gas 32 diffuses through the capillary membrane fibers 8 and comes into contact with the reagent 18 within. The reagent 18 contains an alkaline solution of hydrogen peroxide and a chemiluminescent reactant. Luminol is preferably used as the chemiluminescent reactant in the reagent 18, but any analogous substance, such as isoluminol, AHEI, ABEI, ABEI-NCS, luciferan, cypridina luciferan, CLA, or MCLA may be used. This component of the reagent 18 is responsible for the chemiluminescent reaction that detects $NO_2$. A chemiluminescent reaction is a chemical reaction in which light is emitted. It is known that the reaction of $NO_2$ with a luminol/hydrogen peroxide solution is chemiluminescent. Consequently, the presence and concentration of $NO_2$ in the gas 32 within the chamber 70 is ascertained by the amount of light detected from this chemiluminescent reaction.

The reagent 18 is alkaline. To further minimize the undesirable effects of carbon dioxide, the reagent 18 is buffered. The reagent 18 is partly composed of water. Water reacts with carbon dioxide to form carbonic acid. Consequently, carbon dioxide will render the reagent 18 more acidic, which may- alter the chemiluminescent reaction in a manner that interferes with the detection of $NO_2$. By buffering the reagent 18, the concentration of $NO_2$ in the gas 32 may be more accurately measured. Preferably, the reagent 18 is buffered with a mixture of carbonate and bicarbonate at a 0.05 to 0.5 molar concentration.

The reagent 18 also includes hydrogen peroxide, preferably in substantially a 0.05 molar concentration. The hydrogen peroxide was found experimentally to enhance the chemiluminescent reaction between nitrogen dioxide and luminol by a factor of approximately twenty. Because hydrogen peroxide tends to slowly oxidize luminol in a reaction catalyzed by trace concentrations of metal ions, it is preferred to keep the hydrogen peroxide separate from the luminol until immediately before the gas 32 is tested. Referring to FIG. 1, the luminol, hydrogen peroxide and water are preferably kept separate until they are used.

The presence of carbon dioxide in the gas 32 causes error in the measurement of $NO_2$, especially at concentrations of one percent or higher, due to the contents of the reagent 18. Carbon dioxide can interfere with $NO_2$ measurement in three ways. First, carbon dioxide dissolves in water to form carbonic acid, which lowers the pH of the solution. Reducing the solution pH decreases the apparent amount of $NO_2$ measured, because the reaction of luminol with $NO_2$ is more efficient at high pH. This interference can be minimized or eliminated by buffering the reagent solution, as discussed in more detail below. Second, carbon dioxide reacts with hydrogen peroxide to form peroxycarbonates, which decompose to highly reactive radical anions capable of oxidizing luminol. This oxidizing reaction causes chemiluminescence, thereby increasing the apparent amount of $NO_2$ measured. The scrubber 100 substantially removes carbon dioxide from the gas 32, thereby minimizing any interaction between the reagent 18 and carbon dioxide. As stated above, the scrubber 100 substantially removes nitrogen dioxide from the gas 32 as well, thereby substantially negating the presence of ambient nitrogen dioxide as a source of error. Third, dissolved carbon dioxide in the alkaline luminol solution will alter its pH and reduce the standing background signal from the luminol solution from the expected level. By substantially removing carbon dioxide from the gas 32, as well as buffering the reagent solution, the effect of carbon dioxide on the standing background signal from the luminol solution is minimized or eliminated.

The reagent 18 is alkaline. To further minimize the undesirable effects of carbon dioxide, the reagent 18 is buffered. The reagent 18 is partly composed of water. Water reacts with carbon dioxide to form carbonic acid. Consequently, carbon dioxide will render the reagent 18 more acidic, which may alter the chemiluminescent reaction in a manner that interferes with the detection of $NO_2$. By buffering the reagent 18, the concentration of $NO_2$ in the gas 32 may be more accurately measured. Preferably, the reagent 18 is buffered with a mixture of carbonate and bicarbonate at a 0.05 to 0.5 molar concentration.

Referring back to FIG. 3, the capillary membrane fibers 8 are translucent, enabling the photons produced by the chemiluminescent reaction between $NO_2$ and the reagent 18 to escape. A translucent material is one that transmits light. Consequently, a transparent material, which transmits light without appreciable scattering, is here defined as a subset of the set of translucent materials. As stated above, the capillary membrane fibers 8 are preferably composed of polypropylene.

Referring to FIGS. 1 and 3, photodetector 14 is located adjacent the window 27. In a preferred embodiment, an O-ring 29 substantially encircles the window 27 on the outer surface of the gas exchange module 26. The photodetector 14 is mounted against the window 27, preferably by screwing the photodetector 14 onto the gas exchange module 26 using a plurality of screw holes 31. The use of screws allows for easy removal of the photodetector 14 for changing it out or cleaning it, and allows for application of pressure to the photodetector 14 to seat it against the O-ring 29. By seating the photodetector 14 against the O-ring 29, ambient light is substantially prevented from entering the photodetector 14. In an alternate embodiment, no window 27 is provided in the gas exchange module 26; rather, the photodetector 14 is directly exposed to the chamber 70, and the O-ring 29 provides the additional function of sealing the gas 32 within the chamber 70. Preferably, the photodetector 14 is a photomultiplier tube. However, the photodetector may be a photodiode or other device for detecting photons and reporting photon detection in digital or analog form. The photodetector 14 measures the intensity of light emitted from the fiber bundle 6 as a result of the chemiluminescent reaction between $NO_2$ and the reagent 18. Thus, the measured intensity of light is proportional to the amount of $NO_2$ in the gas 32. The amount of $NO_2$ in the gas 32 is itself proportional to the amount of NO initially in the gas 32; that proportion is given by FIG. 3 and varies depending on the ambient humidity.

Figure 4:
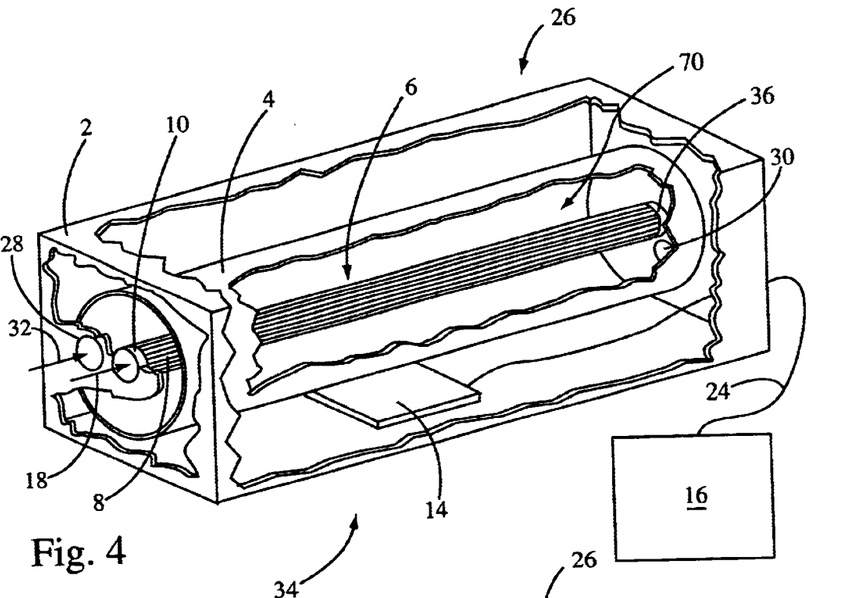
FIG. 4 is a perspective view of an alternate embodiment of a gas exchange module.

In an alternate embodiment, shown in FIG. 4, the gas exchange module 26 is completely opaque, and includes a translucent plenum 4. The photodetector 14 is mounted inside the gas exchange module 26; the opacity of the gas exchange module prevents outside light from striking the photodetector 14. The photodetector 14 is mounted in the gas exchange module 26 in such a way as to view photon emission through the capillary membrane fibers 8.

The nitric oxide gas detector 1 is preferably calibrated by the operator before each use, such that the measured concentration of $NO_2$ can be converted to a measurement of NO. In one method of calibration, gas containing a known concentration of NO is passed through the nitric oxide gas detector 1, and the amount of light thus emitted through the fiber bundle 6 is measured. This light intensity corresponds to the known concentration of NO. By repeating the process with different known concentrations of NO, interpolation may be performed manually or automatically, allowing the measurement of NO concentration in the gas 32. Other methods of calibration are well known to those of ordinary skill in the art.

The luminol/hydrogen peroxide solution will react with oxygen and trace amounts of metal ions in a chemiluminescent reaction. Consequently, a small number of photons are produced in the fiber bundle 6 as a result of oxygen and unavoidable metal contamination of the reagent 18, creating an elevated background signal. Fluctuations in that background contribute to noise in the measurement. However, this amount of background noise is typically small enough to allow measurement of $NO_2$ to a concentration of one part per billion or less.

The photodetector 14 transmits information regarding the intensity of light detected to a monitoring device 16. Preferably, a cable 24 is used to transmit this information. However, the photodetector may transmit information regarding light intensity to a monitoring device 16 by wireless transmission without diminishing the functionality of the invention. Preferably, the monitoring device 16 is a computer capable of recording and displaying the light intensity information it receives from the photodetector 14. However, any device capable of recording, displaying, or manipulating the information received from the photodetector 14 may be used. The nitric oxide gas detector 1 is calibrated such that a given intensity of light measured by the photodetector 14 corresponds to a specific concentration of $NO_2$ in the gases sampled within the chamber 70. Such calibration is well known, and may be readily performed by those of ordinary skill. Consequently, the measuring device 16 can convert light intensity measurements from the photodetector 14 to $NO_2$ concentration levels in the sampled gas 32. Alternatively, the measuring device 16 can store the light intensity information transmitted from the photodetector 14 for later conversion to nitric oxide concentration data.

In an alternate embodiment, the monitoring device 16 may be included in the photodetector 14 or attached to the photodetector 14 within the nitric oxide gas detector 1. Such a monitoring device may be an application-specific integrated circuit (ASIC), a microprocessor, or another device for converting light intensity measurements to nitric oxide concentration data.

In an alternate embodiment, gas 32 flows through the capillary membrane fibers 8 and the reagent 18 flows through the chamber 70. In this embodiment the walls of the capillary membrane fibers need not transmit light, as the chemiluminescent reaction between the reagent 18 and the $NO_2$ molecules takes place in the chamber 70, rather than in the capillary membrane fibers 8.

Figure 5:
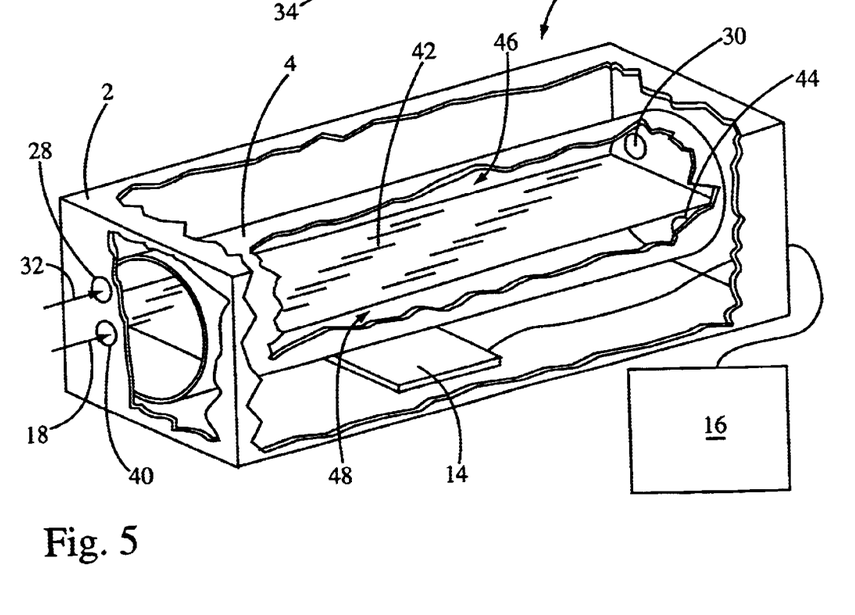
FIG. 5 is a perspective view of an alternate embodiment of a gas exchange module utilizing a membrane.

In an alternate embodiment of the gas exchange module 26, a membrane is used for gas exchange instead of translucent capillary membrane fibers 8. Referring now to FIG. 5, a membrane 42 divides the interior of the gas exchange module 26 into two separate spaces, a first space 46 and a second space 48. The first space 46 and the second space 48 need not enclose equal volumes. Gas 32 enters the first space 46 within the gas exchange module 26 in the gas exchange module 26 through the inlet port 28. The reagent 18 enters the second space 48 in the gas exchange module 26 through a second inlet port 40.

Nitrogen dioxide from the gas 32 within the first space 46 passes through the membrane 42 into the reagent 18 in the second space 48. The criteria for selecting a material and a thickness for the membrane 42 are the same as apply to the capillary membrane fibers 8 in the first embodiment above. The chemiluminescent reaction between $NO_2$ and the reagent 18 occurs within the second space 48.

Figure 6:
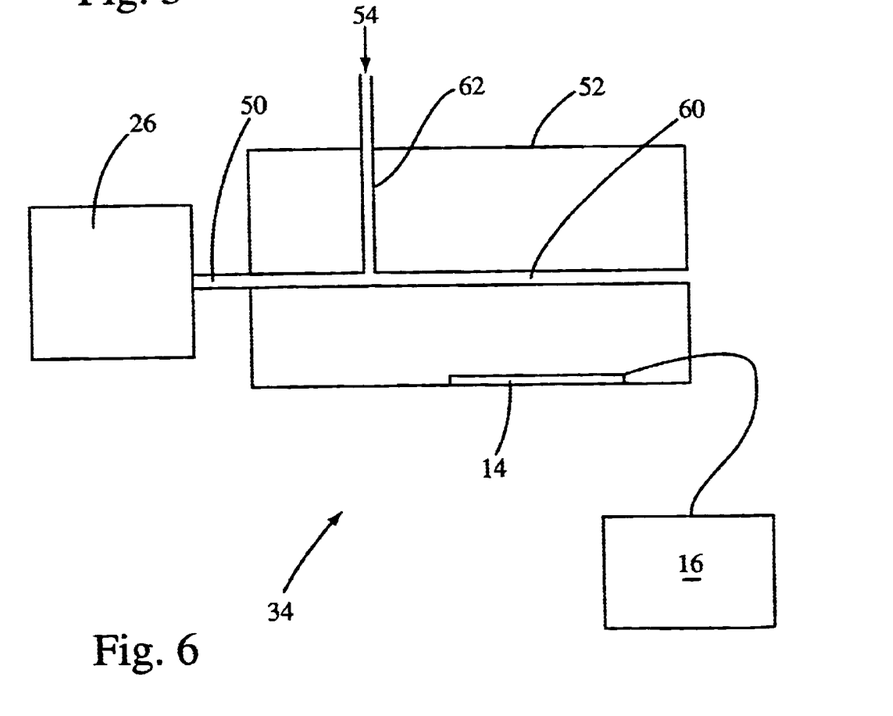
FIG. 6 is a perspective view of an alternate embodiment of the nitric oxide gas detector in which the gas exchange module is separated from the chamber in which chemiluminescence occurs.

Referring to FIG. 6, in an alternate embodiment of the nitric oxide gas detector 1, the chemiluminescent reaction between $NO_2$ and the reagent 18 does not occur within the gas exchange module 26. The gas exchange module 26 operates as disclosed above, with the exception that the reagent 18 does not contain a chemiluminescent reactant. Rather, the reagent 18 preferably comprises a buffered alkaline peroxide solution. Because no chemiluminescent reactant is present in the reagent 18, the chemiluminescent reaction does not take place in the gas exchange module 26. Nitrogen dioxide within the gas 32 in the gas exchange module 26 diffuses into the reagent 18. A tube 50 exits the gas exchange module. The tube 50 is not permeable to NO or $NO_2$ gas or to the reagent 18 within, because introduction of NO or $NO_2$ gas into the tube 50 after the gas exchange module 26 would create a measurement error. The tube 50 enters an opaque housing 52. Within the opaque housing 52, a chemiluminescent reactant 54 such as luminol is introduced through a second tube 62 into the reagent 18 within tube 50. The reaction between the chemiluminescent reactant 54 and the $NO_2$ in the buffered alkaline peroxide solution then begins. A segment 60 of the tube 50 downstream of the intersection of the tube 50 and the second tube 62 is translucent. Light from the chemiluminescent reaction travels through the segment 60, striking the photodetector 14. The photodetector 14 then transmits data to the measuring device 16, as disclosed above for the primary embodiment of the nitric oxide gas detector 34.

Second Preferred Embodiment

In a second preferred embodiment, the scrubber 100, the moisture exchanger 150 and the converter unit 200 are not used. Instead, nitric oxide is measured directly.

Referring to FIG. 4, an opaque enclosure 2 may be seen. The opaque enclosure 2 and its contents are referred to as the gas exchange module 26. Such a gas exchange module 26 was previously described in part above, with reference to its use as an alternate gas exchange module 26 in the preferred embodiment. A gas 32 in which the presence or concentration of nitric oxide is desired to be measured enters the gas exchange module 26 through an inlet port 28 in a wall of the opaque enclosure 2. The inlet port 28 leads to a chamber 70 that forms part of the interior of a plenum 4. To produce a flow of gas 32 into the inlet port 28, a vacuum pump or other suction device may be attached to an outlet port 30. Preferably, the outlet port 30 is located at the opposite end of the plenum 4 from the inlet port 28. However, the outlet port 30 may be placed at any location on the plenum 4 which allows the gas 32 to be sampled to enter the plenum 4 and substantially replace the ambient gas previously reposing in the plenum 4. Alternatively, the gas exchange module 26 may be placed in line or in parallel with a gas line or duct, such that the flow of gas through such gas line or duct impels gas 32 into the inlet port 28 and out of the outlet port 30. The gas 32 is expected to be exhaled human breath. The presence of nitric oxide in exhaled human breath can be a useful diagnostic tool for some ailments.

After the gas 32 has entered the plenum 4 within the gas exchange module 26, the gas 32 comes into contact with one or more capillary membrane fibers 8. Preferably, one or more capillary membrane fibers 8 are organized into a fiber bundle 6. However, the capillary membrane fibers 8 may extend into the plenum 4 independently of one another. Preferably, the fiber bundle 6 is composed of approximately fifty capillary membrane fibers 8. These capillary membrane fibers 8 are preferably substantially parallel within the fiber bundle 6, but they may be twisted or wrapped together into a fiber bundle 6. Preferably, the capillary membrane fibers 8 extend through substantially the entire length of the plenum 4. Each capillary membrane fiber 8 is connected at one end to an inlet connector 10 and at the other end to an outlet connector 36. One side of the inlet connector 10 is connected to one end of each of the capillary membrane fibers 8 that compose the fiber bundle 6. Preferably, the connection between each capillary membrane fiber 8 and the inlet connector 10 is accomplished by epoxy adhesive. However, the connection may be accomplished by any means which do not substantially restrict flow of a reagent 18 from the inlet connector 10 into the capillary membrane fibers 8. The other side of the inlet connector 10 possesses at least one opening for the reagent 18 to enter, and provides for more convenient operation by an operator, who does not have to make individual small-scale connections to each capillary membrane fiber 8. The capillary membrane fibers 8 attach to the outlet connector 36 in the same manner, and the outlet connector 36 also possesses at least one opening for the reagent 18 to exit.

As shown in FIG. 4, the inlet connector 10 and the outlet connector 36 are attached to the walls of the opaque enclosure 2. Also as shown in FIG. 4, each end of the plenum 4 is attached to a wall of the opaque enclosure 2. However, any structural configuration may be used that supports the plenum 4 and the fiber bundle 6 within the opaque enclosure 2.

The reagent 18 flows into the gas exchange module 26 through the inlet connector 10, from there flowing into the capillary membrane fibers 8 composing the fiber bundle 6. The reagent 18 may be induced to flow into the gas exchange module 26 by gravity, by pumping, by suction, or by any other means which can induce a sufficient flow rate of the reagent 18.

The capillary membrane fibers 8 are constructed as disclosed above with regard to the preferred embodiment. Each capillary membrane fiber 8 has a wall 22 composed of a porous material sufficiently thin to allow gaseous NO molecules to pass through, but not so thin or porous that the reagent 18 leaks through the capillary membrane fiber 8. Nitric oxide in the gas 32 is thus brought into contact with the reagent 18 within the capillary membrane fibers 8.

As discussed above, the presence of carbon dioxide in the gas 32 can cause error in the measurement of nitric oxide in the gas 32. This effect is small and relatively constant at atmospheric concentrations of carbon dioxide and nitric oxide, and typically can be ignored. However, the effect of carbon dioxide on the reagent 18 must be minimized when the concentration of carbon dioxide in the gas 32 rises to above approximately one percent. An example is the measurement of nitric oxide in human breath, which is approximately five percent carbon dioxide. To properly measure nitric oxide levels in a gas 32 with such a high level of carbon dioxide, its effect must be minimized.

When the scrubber 100 is not used, as in the second preferred embodiment, other means may be used to minimize the effect of carbon dioxide. Carbon dioxide may be removed from the sample gas by other physical means such as the addition of gas with a high carbon dioxide concentration to raise the level of the background signal above the carbon dioxide concentration of the sample. The effects or carbon dioxide can also be minimized by adding to the reagent 18 other chemicals that react rapidly with carbon dioxide as compared to luminol, such as, but not limited to, carbonic anhydrase. The effect of carbon dioxide may also be reduced by other methods such as measuring the effect of carbon dioxide alone and subtracting that effect from the combined measurement.

The reagent 18 is as disclosed above with regard to the preferred embodiment. To reduce the undesirable effects of carbon dioxide, the reagent 18 is preferably buffered. The reagent 18 is partly composed of water. Water reacts with carbon dioxide to form carbonic acid. Consequently, carbon dioxide will render the reagent 18 more acidic. At a high concentration of carbon dioxide, such as that present in human breath, this acidification becomes significant enough to alter the chemiluminescent reaction in a manner that interferes with the detection of nitric oxide. Therefore, to accurately measure the concentration of nitric oxide in a gas mixture containing a high concentration of carbon dioxide, the reagent 18 must be buffered. Preferably, the reagent 18 is buffered with a mixture of carbonate and bicarbonate at a 0.05 to 0.5 molar concentration. Optionally, carbonic anhydrase is a component of the reagent 18 in the second preferred embodiment. Carbonic anhydrase reacts rapidly with carbon dioxide that comes into contact with the reagent 18, forming carbonic acid ($H_2CO_3$), bicarbonate ($HCO_3^-$) ions, and carbonate ($CO_3^{--}$) ions in solution. By reacting with carbon dioxide molecules that enter the reagent 18, carbonic anhydrase minimizes the measurement error introduced by the presence of carbon dioxide in the gas 32. Preferably, the concentration of carbonic anhydrase used is 1 to 10 milligrams per liter.

The capillary membrane fibers 8 are translucent, enabling the photons produced by the chemiluminescent reaction between nitric oxide and the reagent 18 to escape. A translucent material is one which transmits light. Consequently, a transparent material, which transmits light without appreciable scattering, is here defined as a subset of the set of translucent materials. As stated above, the capillary membrane fibers 8 are preferably composed of polypropylene. Similarly, the plenum 4 is translucent. Preferably, the plenum 4 is composed of a translucent polymer. However, silica or other translucent or transparent materials may be used. A photodetector 14 is located within the opaque enclosure 2. The opaque enclosure 2 prevents outside light from striking the photodetector 14. Preferably, the photodetector 14 is mounted to an interior wall of the opaque enclosure 2. However, the photodetector 14 may be mounted to the plenum 4 or to any other structure within the opaque enclosure 2 where the photodetector 14 can view photon emission from the fiber bundle 6. Preferably, the photodetector 14 is a photomultiplier tube. However, the photodetector may be a photodiode or other device for detecting photons and reporting photon detection in digital or analog form. The photodetector 14 measures the intensity of light emitted from the fiber bundle 6 as a result of the chemiluminescent reaction between nitric oxide and the reagent 18.

The luminol/hydrogen peroxide solution will react with oxygen and trace amounts of metal ions in a chemiluminescent reaction. Consequently, a small number of photons are produced in the fiber bundle 6 as a result of oxygen and unavoidable metal contamination of the reagent 18, creating an elevated background signal. Fluctuations in that background contribute to noise in the measurement. However, the amount of background noise is small enough to allow measurement of nitric oxide to a concentration of one part per billion or less.

The photodetector 14 transmits information regarding the intensity of light detected to a monitoring device 16. Preferably, a cable 24 is used to transmit this information. However, the photodetector may transmit information regarding light intensity to a monitoring device 16 by wireless transmission without diminishing the functionality of the invention. Preferably, the monitoring device 16 is a computer capable of recording and displaying the light intensity information it receives from the photodetector 14. However, any device capable of recording, displaying, or manipulating the information received from the photodetector 14 may be used. The nitric oxide gas detector 34 is calibrated at the factory or by the user, such that a given intensity of light measured by the photodetector 14 corresponds to a specific concentration of nitric oxide in the gases sampled within the plenum 4. Consequently, the measuring device 16 can convert light intensity measurements from the photodetector 14 to nitric oxide concentration levels in the sampled gas 32. Alternatively, the measuring device 16 can store the light intensity information transmitted from the photodetector 14 for later conversion to nitric oxide concentration data. The photodetector 14 is enclosed within the opaque enclosure 2. Preferably, the photodetector 14 is located in close proximity to the plenum 4. However, the photodetector 14 may be placed in contact with the plenum 4 if such contact will not interfere with the operation of the photodetector 14. Further, the photodetector 14 may be placed further from the tube 14, as long as light from the chemiluminescent reactions in the fiber bundle 6 can reach it.

In an alternate embodiment, the monitoring device 16 may be included in the photodetector 14 or attached to the photodetector 14 within the opaque enclosure 2. Such a monitoring device may be an application-specific integrated circuit (ASIC), a microprocessor, or another device for converting light intensity measurements to nitric oxide concentration data.

In an alternate embodiment, gas 32 flows through the capillary membrane fibers 8 and the reagent 18 flows through the plenum 4. In this embodiment the walls of the capillary membrane fibers need not transmit light, as the chemiluminescent reaction between the reagent 18 and the nitric oxide molecules takes place in the plenum 4, rather than in the capillary membrane fibers 8.

In an alternate embodiment of the gas exchange module 26, a membrane is used for gas exchange instead of translucent capillary membrane fibers. Referring now to FIG. 5, a membrane 42 divides the interior of the plenum 4 into two separate spaces, a first space 46 and a second space 48. Such a gas exchange module 26 was previously described in part above, with reference to its use as an alternate gas exchange module 26 in the preferred embodiment. The first space 46 and the second space 48 need not enclose equal volumes. Gas 32 enters the first space 46 within the plenum 4 in the gas exchange module 26 through the inlet port 28. The reagent 18 enters the second space 48 in the plenum 4 through a second inlet port 40.

Nitric oxide from the gas 32 within the first space 46 passes through the membrane 42 into the reagent 18 in the second space 48. The criteria for selecting a material and a thickness for the membrane 42 are the same as apply to the wall 22 in the first embodiment above. The chemiluminescent reaction between nitric oxide and the reagent 18 occurs within the second space 48.

The membrane 42 need not be translucent. However, the plenum 4 must be translucent in order for light to escape and be sensed by the photodetector 14. The photodetector 14 must be located within the gas exchange module 26 such that light from the chemiluminescent reactions in the second space 48 can reach it. Preferably, the photodetector 14 is attached to the opaque enclosure 2 in close proximity to the plenum 4 on the same side as the second space 48, particularly if the membrane 42 is opaque.

Referring to FIG. 6, in an alternate embodiment of the nitric oxide gas detector 2, the chemiluminescent reaction between nitric oxide and the reagent 18 does not occur within the gas exchange module 26. The gas exchange module 26 operates as disclosed above, with the exception that the reagent 18 does not contain luminol or carbonic anhydrase. Rather, the reagent 18 is simply composed of water and a buffered alkaline peroxide solution. Because luminol is not present in the reagent 18, the chemiluminescent reaction does not take place in the gas exchange module 26. Consequently, neither the plenum 4 nor the capillary membrane fibers 8 need be translucent. Alternately, if the membrane 42 is used for gas exchange, it need not be translucent. Further, the enclosure 2 need not be opaque. Nitric oxide within the gas sampled in the gas exchange module diffuses into the buffered alkaline peroxide solution. Finally, the photodetector 14 is not present within the gas exchange module 26.

A tube 50 exits the gas exchange module 26. Such a gas exchange module 26 has been previously described in part above. A buffered alkaline peroxide solution travels through the tube 50, carrying nitric oxide and its reaction products in solution from the gas exchange module 26. The tube 50 enters an opaque housing 52. Within the opaque housing 50, luminol 54 is introduced through a second tube 62 into the buffered alkaline peroxide solution within tube 50. The chemiluminescent reaction between the luminol 54 and the nitric oxide in the buffered alkaline peroxide solution then begins. Consequently, a segment 60 of the tube 50 downstream of the intersection of the tube 50 and the second tube 62 must be translucent. Light from the chemiluminescent reaction travels through the segment 60, striking the photodetector 14. The photodetector 14 then transmits data to the measuring device 16, as disclosed above for the primary embodiment of the nitric oxide gas detector 34. The tube 50 cannot be permeable to nitric oxide gas or to the reagent within. Introduction of nitric oxide gas into tube 50 after the gas exchange module 26 would create a measurement error.

Optionally, a solution of carbonic anhydrase may be introduced into the tube 50. This is preferably accomplished through the second tube 62 along with the introduction of luminol into the tube 50. However, carbonic anhydrase may be introduced separately into the tube 50 at any location upstream from the intersection of the second tube 62 with the tube 50. Addition of carbonic anhydrase is desirable when nitric oxide concentration is to be measured in an environment containing a high level of carbon dioxide. The carbonic anhydrase 56 need not be introduced into the tube 50 when nitric oxide is to be measured in an environment containing a low level of carbon dioxide.

A preferred nitric oxide gas detector and many of its attendant advantages have thus been disclosed. It will be apparent, however, that various changes may be made in the form, construction, and arrangement of the parts without departing from the spirit and scope of the invention, the form hereinbefore described being merely a preferred or exemplary embodiment thereof. Therefore, the invention is not to be restricted or limited except in accordance with the following claims and their legal equivalents.

What is claimed is:

1. A method for measuring the concentration of nitric oxide in exhaled human breath gas, comprising the steps of:

provided a reagent that participates in a chemiluminescent reaction with nitric oxide, said reagent including carbonic anhydrase;

inducing a flow of said reagent within a plurality of translucent capillary membrane fibers composed of material sufficiently thin and porous to allow gaseous nitric oxide molecules to diffuse into the translucent capillary membrane fiber or fibers and sufficiently hydrophobic to prevent the reagent from substantially diffusing out of the translucent capillary membrane fiber or fibers;

passing the gas to be sampled over the surface of the translucent capillary membrane fiber or fibers; and measuring the amount of light generated by the chemiluminescent reaction between the reagent and the gas which has passed through the walls of the translucent capillary membrane fiber or fibers.

* * * * *